United States Patent [19]

Pinto

[11] 4,149,940
[45] Apr. 17, 1979

[54] METHANOL

[75] Inventor: Alwyn Pinto, Stockton-on-Tees, England

[73] Assignee: Imperial Chemical Industries Limited, London, England

[21] Appl. No.: 860,949

[22] Filed: Dec. 15, 1977

[30] Foreign Application Priority Data

Dec. 22, 1976 [GB] United Kingdom ............... 53505/76

[51] Int. Cl.² ..................... C07C 29/16; C07C 29/30; B01D 3/40
[52] U.S. Cl. ........................................ 203/25; 203/85; 203/96; 203/DIG. 8; 203/DIG. 19; 203/DIG. 23; 260/449.5; 260/450; 568/913
[58] Field of Search ............... 260/449.5, 450, 643 R; 203/96, 97, 92, 93, 76, 79, 83, 85, 27, 23, 21, 25, DIG. 8, DIG. 23, DIG. 19

[56] References Cited

U.S. PATENT DOCUMENTS

| | | | |
|---|---|---|---|
| 2,437,649 | 3/1948 | Milner | 203/96 |
| 3,186,145 | 6/1965 | Pelton et al. | 260/449.5 |
| 3,230,156 | 1/1966 | Katzen | 203/37 |
| 3,406,100 | 10/1968 | Karafian | 203/79 |
| 3,442,770 | 5/1969 | Wentworth et al. | 203/85 |
| 3,471,371 | 10/1969 | Nagy et al. | 203/96 |
| 3,597,465 | 8/1971 | Karafian et al. | 260/449.5 |

FOREIGN PATENT DOCUMENTS

| | | |
|---|---|---|
| 1272798 | 5/1972 | United Kingdom. |
| 1309872 | 3/1973 | United Kingdom ................. 260/449.5 |
| 1316705 | 5/1973 | United Kingdom. |

Primary Examiner—Wilbur L. Bascomb, Jr.
Attorney, Agent, or Firm—Cushman, Darby & Cushman

[57] ABSTRACT

A methanol production process including synthesis gas generation, methanol synthesis and methanol distillation includes an autonomous system in which low pressure steam is raised by heat exchange with a fluid stream at 120°–300° C. in the process, the low pressure steam is used as live steam to heat at least distillation column in the distillation section and bottoms water from a distillation column in that section is used as feed to the autonomous steam system.

11 Claims, 1 Drawing Figure

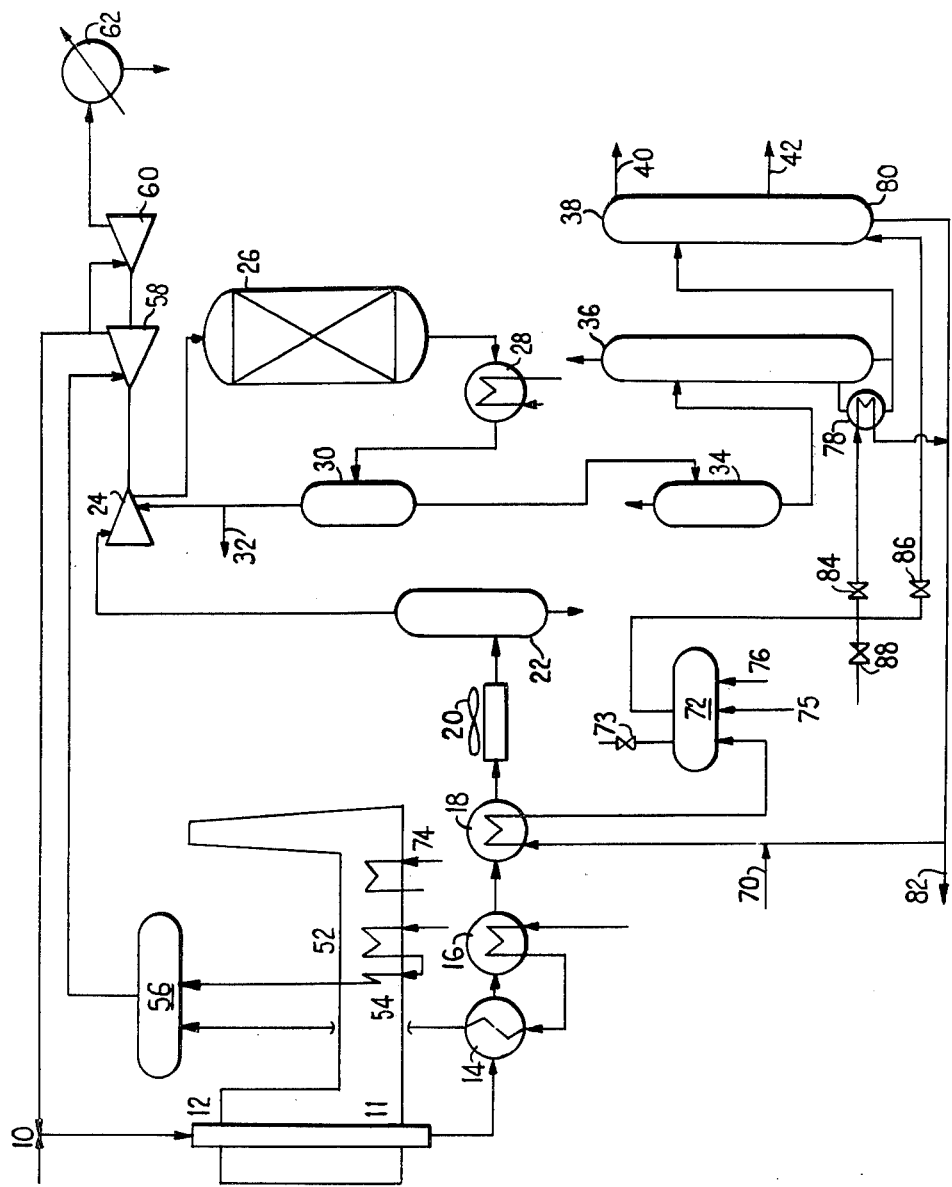

METHANOL

This invention relates to methanol and in particular to a methanol production process characterised by the means by which heat is provided for distillation.

A methanol production process consists essentially of three sections, namely generation of synthesis gas, catalytic reaction of synthesis gas to produce crude methanol and purification of the crude methanol by distillation, each characterised by energy relationships. Thus synthesis gas generation, which includes reaction of a carbonaceous feedstock with steam at high temperature (such as 700°–1200° C.), requires the supply of high grade heat and can afford a high grade recovery in cooling its product. Synthesis usually requires gas compression (a large energy input) but can afford an intermediate grade heat recovery in cooling reacted gas. Distillation requires a large input of low grade heat.

In modern methanol production processes the energy relationships of the three sections have been integrated in various ways in order to minimise the overall energy input per unit of purified product methanol. A common heat recovery involves cooling synthesis gas in a boiler generating high pressure steam, letting down the steam in a pass-out turbine driving the synthesis gas compressor, and using the passed-out steam partly as process steam for synthesis gas generation and partly in turbines exhausting at low pressure into the re-boilers of the distillation section and/or in condensing turbines. The heat evolved in synthesis is recovered in one process as intermediate pressure steam, which is then let down in a turbine, and in another as hot feed water for the generation section boiler. Each of these processes involves a complicated steam system.

In the process described in U.K. specification No. 1,280,438 it has been proposed to provide heat for the distillation section independently of the high-pressure or intermediate pressure steam system by bringing partly-cooled crude synthesis gas or reacted synthesis gas into heat exchange in distillation column re-boilers, either by feeding such gases directly to the re-boilers or by way of a circulating fluid. This effects a useful low-grade heat recovery but either has the disadvantages lengthy piping of highly inflammable gas under pressure, difficulty in measuring the heat input to the distillation and a large pressure-relieving system to avoid a gas leak into the column, or else entails the expense of the separate cooling fluid circuit carrying only sensible heat.

We have devised a new system for providing heat for the distillation, in which the above-mentioned defects are largely avoided and other advantages secured.

According to the invention a methanol production process comprises a synthesis gas generation section, a synthesis section and a distillation section and is characterised in that in the distillation section at least one distillation column is heated by live steam generated at low pressure by heat exchange of column bottoms water with a fluid stream at a temperature in the range 120°–300° C. in the synthesis gas generation section or the synthesis section of the process.

The plant in which the process is carried out is a further aspect of the invention.

The steam generation procedure is "autonomous", that is, is separate from other steam generation systems that may be present in the process. Since its source of water is column bottoms, it does not require a water pre-treatment installation. Since its water feed is not used in other steam systems in the plant, the standard of purity required is a local one and thus an objection to live steam heating of columns, namely that condensate is not recoverable, is not encountered. The process is especially advantageous when the column from which the bottoms water is taken is operated with at least one off-take for a purge stream containing a component of higher boiling point than methanol, since then the content of such components in the bottoms water is very low and may be effectively zero.

The column from which the bottoms water is taken is very suitably one in which is distilled a mixture consisting essentially of methanol, water and ethanol, the proportions of water being for example 8–30% w/w and the proportion of ethanol for example up to 0.5% w/w, and in which the feed level is such that the methanol to water ratio is maintained substantially constant over a region of the column and a stream enriched in ethanol is taken off from a point near one end of the region. In such a column the region can be set up by feeding the mixture to the column at a point at which, if the column were in equilibrium operation, the water content would be lower than in the mixture, and an ethanol-enriched stream is withdrawn from the liquid present at a level below the feed point. Such a distillation operation is described more fully in our U.K. specification No. 1,373,159.

In the process of the invention the water in the column bottoms can be derived entirely from the steam injected live as the source of heat if the feed to the column is water-free. More commonly the feed contains water. One example of such a feed is a crude stream produced by reacting a mixture of carbon monoxide and carbon dioxide with hydrogen, as in most synthesis processes over a copper-containing catalyst. The column handling such a feed should of course be one that produces water bottoms, rather than so-called "topping column" producing aqueous methanol bottoms, and can be one that produces pure product methanol as a high side stream. Such a column can, however, be heated by the live steam. Likewise a column effecting water-extractive distillation or effecting coarse distillation to bring the water content of water-extractive bottoms from 40–60 or even 80–95% w/w down to for example 8–30% w/w is not suitable as a source of water for the steam generation but may be heated by the live steam. A column fed with the bottoms of such a water-extractive or coarse distillation is suitable as a source of water for steam generation. In a typical process according to the invention a topping column is fed with a mixture of low or even zero water content and heated by live steam, or with a mixture of considerable water content, for example 15–30% w/w and heated by indirect heat exchange, and its bottoms are distilled in a "refining" column or columns heated by live steam and providing bottoms water. The water in the crude feed stream can have been introduced by employing water-scrubbing, instead of or in addition to condensation and separation, to remove methanol from reacted synthesis gas in the synthesis section.

When the column feed contains water, a purge of water from the low pressure steam system equal to the rate of feed of water to the column is maintained. When the column feed contains impurities that come out in the bottoms water, for example when the methanol synthesis section employs a zinc-chrome catalyst at high temperature and pressure and thus produces a more impure crude methanol than a copper-catalysed synthesis, the purge prevents excessive build-up of such impurities. If necessary, a feed of water to the steam system can be maintained in order to increase the purge rate and limit build-up of impurity levels.

Among the process streams at 120°-300° C. from which low pressure steam can be raised are the following:

(a) newly generated synthesis gas after cooling from its generation temperature (over 400° C. for a shift reaction, 700°-1200° C. for a steam reforming or partial oxidation reaction) in high grade heat recoveries such as steam superheating, feedstock preheating and generation of high pressure steam at 40-120 atm. abs.;

(b) furnace flue gas when synthesis gas generation is by endothermic catalytic steam reforming of a hydrocarbon, after cooling such gas in high grade heat recoveries;

(c) reacted methanol synthesis gas, after one or more other heat exchanges such as feed gas preheating, medium pressure steam generation and boiler feed water heating.

Supplementary steam can be raised from other steam systems in the process.

In each of these steam raising procedures the heat exchange with water can be indirect. In addition, if the newly generated synthesis gas is at a high enough pressure, for example over 7 atm. abs., and contains steam, the low pressure steam can be generated by injecting water into it, removing the resulting hot water under a pressure too high to permit boiling and then decreasing the pressure so that the water partly boils; the unboiled water is then pumped back to the direct heat exchange, conveniently mixed with the column bottoms water. Whichever steam raising procedure is used, the steam can, if desired, be superheated by heat exchange with a suitable process stream.

Freshly generated synthesis gas is the preferred source of heat for low pressure steam generation since it is typically at a pressure high enough to afford better heat transfer coefficient than furnace flue gas, yet not so high as to require expensive equipment, such as would be needed for reacted synthesis gas.

The temperature of the gas stream in heat exchange with which the low pressure steam is generated is preferably in the range 125° to 200° C. Since live steam is used in distillation, the steam pressure can be lower (suitably at 10 to 30, especially 14 to 25 psig) than when indirect heat exchange re-boilers are used. Consequently the final temperature of the gas stream can be lower than was previously thought practicable and the energy consumption per metric ton of methanol product is correspondingly less. A saving of about $0.2 \times 10^6$ BTU per metric ton is possible.

The synthesis gas generation section of the process will normally involve steam reforming or partial oxidation of a carbonaceous feedstock. Such a section with its heat recoveries are described in our co-pending U.K. application No. 29620/74, (Ser. No. 1,484,366). That application outlines preferred conditions of heat recovery for the synthesis section when synthesis is at under 300° C. (especially 190°-270° C.) with catalyst containing copper and preferably also zinc oxide and one or more other oxides such as those of aluminium, chromium and vanadium. The pressure is preferably in the range 30-120 atm. abs. However, a methanol synthesis section of the older type, at temperatures of 300°-400° C. and pressures over 200 atm. abs., over a zinc-chrome catalyst, can alternatively be used.

One preferred form of the invention is shown schematically in the accompanying drawing, in which items 10-42 relate to process fluids, 50-62 to the high pressure steam system and 70-88 to low pressure steam system.

The starting materials steam and natural gas are mixed at 10 and passed via a superheater (not shown) in the convective zone of furnace 1 to reformer tubes 12, which contain a nickel-on-refractory steam reforming catalyst, and are heated externally in the radiant zone of furnace 11. The product of catalytic reaction, consisting mainly of carbon oxides, hydrogen and excess steam is cooled from its temperature in the range 700°-900° C. in high pressure waste heat boiler 14, boiler feed water heater 16, low pressure boiler 18 and finally, to below the dewpoint of steam, in cooler 20. Condensate is separated at 22 and the remaining substantially dry gas passed to circulating compressor 24 in which is compressed and mixed with a recycle steam of synthesis gas. The compressed mixed gas is heated to the inlet temperature of methanol synthesis and passed to reactor 26, in which it passes over a copper-zinc oxide-alumina catalyst at an outlet temperature in the range 240°-270° C. and undergoes imconplete reaction to methanol. (For simplicity the means of heating the gas is not shown, nor the means of controlling the temperature of the synthesis catalyst). The reacted gas leaving the catalyst is cooled by known means (not shown: suitably preheating of feed gas and heating of boiler feed water for the high pressure steam system would be used) to a temperature at which low grade heat recovery is possible and passed through low pressure waste heat boiler 28. After final cooling, to below the dewpoint of methanol, the gas is passed to separator 30, from which a recycle gas stream is removed overhead and passed (apart from a small purge stream taken at 32) to an intermediate pressure level in compressor 24. The crude methanol bottoms from separator 30 is let down in pressure in vessel 34, from which gases liberated from solution in the crude methanol are removed overhead. The remaining liquid is heated to about its boiling point in an indirect heat exchanger (not shown) and passed into topping column 36, from which volatile impurities (chiefly dimethyl ether) are taken over-head and aqueous methanol is taken as bottoms. The bottoms liquid contains water from the crude feed; if low-$CO_2$ synthesis gas is used, as in the corresponding process in which synthesis gas is generated by partial oxidation, then topping column 36 can be heated by live steam, which will contribute to the water in the bottom liquid. The liquid is passed into refining column 38 at a plate high enough to produce below the feed plate a region in which the methanol to water ratio is substantially constant. Pure methanol product is taken from an upper plate at 40. A purge stream containing impurities less volatile than methanol is taken at 42, just below the constant ratio region. At the bottom substantially pure water, from the water fed with the aqueous methanol and from the steam, is taken as the feed water for the low pressure steam system.

In the high pressure steam system boiler feed water (which preferably has been preheated by heat exchange with reacted gas leaving reactor 26) is further heated in exchanger 16 in the synthesis gas line, boiled in boiler 14 and passed to steam drum 56. At the same time a parallel supply of the boiler feed water is further heated in economiser 52 and boiler 54 in the flue gas duct of furnace 11 and fed to steam drum 56. Steam from drum 56 is let down in pass-out turbine 58, the exhaust of which is partly fed to the process inlet at 10 and partly let down furtherin condensing turbine 60, from which it passes to condenser 62.

In the low pressure steam system water is fed, if required, at 70 into the recycle water stream and boiled in low pressure boiler 18 feeding steam drum 72. (A dehumidifier, that is a vessel providing direct that exchange by injection of water, could be used instead boiler 18). If desired, a parallel supply of low pressure steam is produced in boiler 74 in the flue gas duct of furnace 11 and fed to steam drum 72 at 75. Further, if desired, a parallel supply of low pressure steam is produced in boiler 28 heated by cooled reacted synthesis gas and fed to steam drum 72 at 76. Although a separate steam drum 72 has been shown it can in practice be provided by a unit integral with one of boilers 18, 28 and 74. Drum 72, whether separate or integral, is equipped with relief valve 73. Steam from drum 72 is divided into a stream fed to topping column re-boiler 78 (using indirect heat exchange, although direct heat exchange can be used: see above), a stream fed to refining column 38 and a control stream. The bottoms liquid of column 38 contains water from the crude methanol, from any steam fed to column 36 and from steam used in heating and is taken off at 80 for recycle to boiler 18 and also boilers 74 and 28 if used. Water is purged at 82 at a rate equal to the feed rate in the crude methanol plus any extra water added at 70. The rate of feed of steam to columns 36 and 38 is controlled by valves 84 and 86 respectively, which are non-return valves. Valve 88 controls the rate of import or export low pressure steam. Thus the rate of heating of the columns can be controlled independently of the inelastic heat flows elsewhere in the process.

I claim:

1. In a methanol production process comprising the steps of generating methanol synthesis gas, synthesizing methanol, recovering crude methanol and purifying the crude methanol by distillation in at least one column in which water is taken as bottoms, the improvement which comprises heating at least one distillation column by live steam generated at low pressure by heat exchange of said bottoms water with at least one fluid stream having a temperature in the range 120° to 300° C. produced during the said generating and synthesizing steps.

2. A process according to claim 1 in which the column from which the bottoms water is taken is operated with at least one off-take for a purge stream containing a component of higher boiling point than methanol.

3. A process according to claim 1 in which the column from which the bottoms water is taken is one fed with the bottoms of a water-extractive distillation or of a coarse distillation decreasing the water content of said bottoms of a water-extractive distillation.

4. A process according to claim 1 in which the column from which the bottoms water is taken is a refining column in which is distilled the bottoms of a topping column fed with a mixture of low or zero water content and heated by live steam.

5. A process according to claim 1 in which the column from which the bottoms water is taken is a refining column in which is distilled the bottoms of a topping column fed with a mixture containing 15-30% w/w of water and heated by indirect heat exchange.

6. A process according to claim 1 in which the fluid stream at 120°-300° C. is newly generated synthesis gas after high grade heat recovery.

7. A process according to claim 1 in which synthesis gas generation is by endothermic catalytic steam reforming of a hydrocarbon and the fluid stream at 120° to 300° C. is flue gas from a furnace supplying heat to said endothermic catalytic steam reforming after high grade heat recovery from such gas.

8. A process according to claim 1 in which the fluid stream at 120°-300° C. is reacted methanol synthesis gas.

9. A process according to claim 1 in which the pressure of the live steam is in the range 14 to 25 psig.

10. A process according to claim 1 in which the methanol synthesis is operated at a temperature under 300° C. and a pressure in the range 300-120 atm. abs., and is catalyzed by a copper-containing catalyst.

11. In a methanol production process comprising the steps of:
generating methanol synthesis gas;
synthesizing methanol;
recovering crude methanol;
purifying crude methanol by distillation in at least one column in which water is taken as bottoms; and
in the course of said generation or said synthesis producing at least one fluid stream having a temperature in the range 120° to 300° C.;
the improvement which comprises:
bringing said bottoms water into heat exchange with at least one of said fluid streams to generate low pressure steam; and
piping said low pressure steam from the said heat exchange to at least one said column in which water is taken as bottoms and injecting the said piped steam live into the liquid at the bottom of the column.

* * * * *